(12) United States Patent
Conrad

(10) Patent No.: US 6,812,341 B1
(45) Date of Patent: Nov. 2, 2004

(54) HIGH EFFICIENCY MRNA ISOLATION METHODS AND COMPOSITIONS

(75) Inventor: Richard C. Conrad, Austin, TX (US)

(73) Assignee: Ambion, Inc., Austin, TX (US)

( * ) Notice: Subject to any disclaimer, the term of this patent is extended or adjusted under 35 U.S.C. 154(b) by 52 days.

(21) Appl. No.: 09/854,412

(22) Filed: May 11, 2001

(51) Int. Cl.$^7$ .............................. C12Q 1/68; C07H 21/02
(52) U.S. Cl. ............................ 536/25.4; 435/7.5; 435/6; 536/23.1; 536/25.5
(58) Field of Search ...................... 435/6, 7.5; 536/23.1, 536/25.4

(56) References Cited

U.S. PATENT DOCUMENTS

| | | | |
|---|---|---|---|
| 5,395,753 A | | 3/1995 | Prakash |
| 5,459,253 A | | 10/1995 | Wolin et al. |
| 5,614,391 A | | 3/1997 | Franciskovich et al. |
| 5,654,147 A | | 8/1997 | Wood et al. |
| 5,759,777 A | * | 6/1998 | Kearney et al. |
| 5,866,429 A | | 2/1999 | Bloch |
| 6,045,996 A | | 4/2000 | Cronin et al. |
| 6,379,898 B2 | * | 4/2002 | Shultz et al. |

FOREIGN PATENT DOCUMENTS

WO    WO 01/81566    11/2001

OTHER PUBLICATIONS

Aviv et al. Purification of Biologically Active Globin messenger RNA by chromatography on Oligothymidylic acid Cellulose PNAS Col. 69 No. 6 1972 pp 1408–1412.*

Jacobs et al. The thermal stability of oligonucleotide duplexes is sequence independent in tetraalkylammonium salt solutions: application to identifying recombinant DNA clones. Nucleic Acids Research vol. 16 No. 10 1998 pp4637–4650.*

Conlan et al. Modulating restriction endonuclease activities and specifications using neutral detergents Biotechniques vol. 27 No. 5 1999 pp955–958.*

Aviv and Leder, "Purification of biologically active globin messenger RNA by chromatography on oligothymidlic acid-cellulose," *Proc. Natl. Acad. Sci. U S A,* 69(6):1408–1412, 1972.

Gitschier et al., "Identification of a midsense mutation in the factor VIII gene of a mild hemophiliac," *Science,* 232(4756):1415–1416, 1986.

Golas et al., "The Effects of the tetraalkylammonium salts on helix–coil transition parameters in natural and synthetic ribo– and deoxyribo–polynucleotides," *Chem–Biol. Interact.,* 30:209–222, 1980.

Jacobs et al., "The thermal stability of oligonucleotide duplexes is sequence indepentend in tetraalkylammonium salt solutions: application to identifying recombinant DNA clones," *Nucleic Acids Res,* 25;16(10):4637–4650, 1988.

Jacobs et al., "Isolation and characterization of genomic and cDNA clones of human erythropoietin," *Nature,* 313(6005):806–810, 1985.

Kuribayashi et al., "A rapid efficient purification of poly(A)–mRNA by oligo(dT)$_{30}$–latex," *Nucleic Acids Res.,* Series 19:61–64, 1988.

Melchior et al., "Alteration of the relative stability of dA · dT and dG · dC base pairs in DNA," *Proc Natl Acad Sci U S A,* 70(2):298–302, 1973.

Nguyen et al., "Smoothing of the thermal stability of DNA duplexes by using modified nucleosides and chaotropic agents," *Nucleic Acids Res.;* 27(6): 1492–1498, 1999.

Rees et al., "Betaine can eliminate the base pair composition dependence of DNA melting," *Biochemistry,* 32(1):137–144, 1993.

Schott and Han, "Effect of symetrical tetraalkylammonium salts on cloud point of nonionic surfactnats," *J. Pharm. Sci.,* 66(2):165–168, 1977.

Shapiro et al, "The binding of small cations to deoxyribonucleic acid. Nucleotide specificity," *Biochemistry,* 8(8):3233–41, 1969.

Wood et al., "Base composition–independent hybridization in tetramethylammonium chloride: a method for complex gene libraries," *Proc Natl Acad Sci U S A,* 82(6):1585–1588, 1985.

Wozney, "Using purified protein to clone its gene," *Methods Enzymol* 182:738–51, 1990.

Sambrook et al., *Molecular Cloning: A Laboratory Manual,* $2^{nd}$ edition, Cold Spring Harbor Laboratory Press, pp. 7.26–7.29, 1989.

* cited by examiner

Primary Examiner—James Ketter
Assistant Examiner—David A. Lambertson
(74) *Attorney, Agent, or Firm*—Fulbright & Jaworski L.L.P.

(57) ABSTRACT

The present invention provides methods and compositions, including kits, for the isolation and purification of mRNA, particularly poly(A) RNA. It concerns the use of isostabilizing salts such as TMAC and TEAC to reduce rRNA carryover during the purification process, thus facilitating the isolation of poly(A) RNA.

36 Claims, 2 Drawing Sheets

HIGH EFFICIENCY MRNA ISOLATION METHODS AND COMPOSITIONS

BACKGROUND OF THE INVENTION

1. Field of the Invention

The present invention relates generally to the field of RNA isolation, more specifically it concerns a faster, more efficient method for the isolation of messenger RNA (mRNA) from total RNA.

2. Description of Related Art

In eukaryotic organisms, one trait shared by all mRNAs is the presence on the 3' end of a stretch of tens to hundreds of adenine (A) residues. This has been used as a means for separating these molecules away from rRNA and other non-mRNA species that lack this "polyA tail." The standard protocol for the selection of polyA$^+$ RNA is based on the method of Aviv and Leder (1972), wherein a short stretch of DNA consisting solely of thymidine (T) residues ("oligo-dT") is affixed to an insoluble matrix. The original procedure used oligo-dT covalently linked to cellulose poured into a column. This is then used as a selective immobilization matrix for mRNA in the sample by setting up conditions that favor formation of RNA-DNA double strands. The total RNA sample is applied to the column in an appropriate salt buffer (originally 0.5 M KCl in 10 mM Tris, pH 7.5), encouraging hybridization to the polyA stretches found solely at the 3' ends of mRNA. The column is then subjected to extensive washing with the application buffer (containing 0.5 M KCl), then a lower-ionic-strength solution (0.1 M KCl), followed by elution of mRNA with 10 mM Tris (pH 7.5). Subsequent modifications on this original procedure have retained the basic process of hybridization to immobilized oligo-dT in approximately 0.5 M salt, but have changed the format from columns to batch procedures to allow the procedure to be performed faster and have used NaCl or LiCl as the salts.

Further changes have been the replacement of cellulose with plastic or glass beads as the immobilization matrix, some of which are impregnated with ferrous material giving them a magnetic quality. This magnetic quality allows such magnetic beads, as they are referred to, to be batch isolated on magnetic stands rather than requiring gravity or centrifugal force to pellet or filter separate. A further wrinkle in the procedure is the use of a biotin-streptavidin linkage in the connection between oligo-dT and bead, where the oligo is biotinylated and the bead is covalently coupled to streptavidin. The hybridization can be performed in solution with this procedure, linking the oligo-dT-mRNA hybrids to the beads in a subsequent step.

This procedure has tended to be an inefficient method for the separation of rRNA from the mRNA. rRNA carryover levels are often high enough to provide the same problems as presented with total RNA, especially for analysis of rare transcripts. In fact, it usually requires two or more passages through a matrix of choice to produce RNA sufficiently low in rRNA levels to provide a useful sample. This requirement for repetitions of the entire selection procedure can lead to several disadvantageous side effects, which can extend the hours required to perform the procedure. Additionally, the representational distribution of various mRNAs may become altered (or more altered), or the unavoidable losses associated with the repeated procedure may reduce the level of the commonly-sought low-abundance messages beyond the limits of detection. While these drawbacks may be tolerable in a research lab, it a major problem in a diagnostic setting where simplicity, speed and reliability are driving characteristics for a viable assay.

Factors affecting the carryover of rRNA have not been thoroughly studied. Remedial measures have been taken with a vague notion of enhancing the "good" interaction in the extended A:T hybrid desired by using low ionic-strength (high-stringency) washes and trying to find more "inert" materials to use as support. Current procedures use washes at lower ionic strength to remove rRNA that is non-specifically bound to the matrix and the oligo dT. To minimize the non-specific binding of rRNA, novel matrix compositions distinct from cellulose have been pursued, using beads made out of synthetic polymers like latex, polystyrene, other plastics, or even glass. A further modification to enable the streamlining of washing routines was the introduction of plastic or glass beads impregnated with magnetite. This enables the capture of all the beads in a microcentrifuge tube by pulling them to the side with a powerful magnet. Supernatants can be aspirated away to the bottom of the tube, leaving very little carryover of each wash.

Isostabilizing agents, such as tetramethylammonium (TMA$^+$) and tetraethylammonium (TEA$^+$) ions and the amino acid betaine, equalize the hydrogen bonding strength of the G-C and A-T base pairs when used at the appropriate concentrations (Jacobs et al., 1988; Jacobs et al., 1985; Gitschier et al., 1986; Melchior et al., 1973; Rees et al., 1993; Wood et al., 1985; Wozney, 1990). However, while tetramethylammonium chloride (TMAC) and tetraethylammonium chloride (TEAC) have been studied with respect to their effect on thermal transition effects on double-stranded nucleic acid (Golas et al., 1980) and have been employed for hybridization generally (U.S. Pat. No. 5,759,777), they have not been used with a mixed RNA population to facilitate mRNA isolation since some of the problems associated with mRNA isolation with existing techniques were unrecognized.

Thus, there is a need to identify the factors affecting mRNA isolation. With this information, compositions and methods for improved separation of mRNA from other RNA molecules can be developed. Such compositions and methods could facilitate mRNA isolation and purification, for example by increasing the speed of the process or increasing the purity of the end product, which is necessary for scientific research, as well as diagnostic and therapeutic purposes.

SUMMARY OF THE INVENTION

The present invention takes advantage of the discovery that some problems with mRNA isolation stems from rRNA carryover that is based not on rRNA interactions with the targetting molecule, oligo-dT, but on rRNA interactions with the targeted molecule, mRNA. While hybridization between oligo-dT and poly(A) RNA is based solely on A:T base-pairing, interactions between rRNA and mRNA involves both A:T and G:C base-pairing. A G:C base pair is stronger than an A:T or A:U base pair, such that the advantage of exact complementation between A and T residues for long stretches (between the targeting molecule and the targeted molecule) are less significant in the face of stronger G:C base pairing between the targeted molecule, mRNA, and contaminating rRNA, even though the stretches may be localized (or shorter) or less exact. Thus, the invention is based on the additional discovery that mRNA isolation is affected by reducing the hybridization between contaminating rRNA and mRNA through the use of an isostabilizing agent, such as TMAC or TEAC salts or the amino acid betaine, which minimizes any difference in bond strength between A:T and G:C basepairs.

The present invention concerns methods, compositions, and kits that facilitate mRNA isolation by increasing the ease or convenience of mRNA isolation, reducing contamination by other non mRNA molecules, increasing the concentration of mRNA, reducing the amount of time to effect mRNA isolation, reducing degradation of RNA in a sample, or any other way that facilitates mRNA isolation.

Thus, in some embodiments of the present invention, methods for purifying mRNA from a sample are contemplated. The term "purifying" refers to the isolation of mRNA, such that the concentration of mRNA compared to other components increases relative to other components, such as other RNA species. Throughout this application, the terms "mRNA" and "poly(A) RNA" are used synonymously since mRNA from most non-bacterial organisms have a poly(A) tail. Any poly(A) RNA from any species is specifically contemplated for isolation using the methods of the present invention. "Poly(A) RNA" includes any RNA species with consecutive "A" residues toward the 3' end of an RNA transcript, including those with greater than 10 "A" residues.

In some embodiments, poly(A) RNA is isolated from a sample by incubating the sample with an isostabilizing salt and a component that selects the poly(A) RNA as the targeted molecule. The component may be a nucleic acid molecule, RNA or DNA, comprising contiguous "T" and/or "U" residues ("poly(T) or poly(U) nucleic acid molecule"). In a method of the invention, a composition including the sample, an isostabilizing salt and a poly(T) or poly(U) nucleic acid molecule is incubated under conditions that allow poly(A) RNA to hybridize with the poly(T) or poly(U) nucleic acid molecule. Subsequently, the poly(T) or poly(U) nucleic acid hybridized to mRNA can be isolated or separated from the remainder of the sample. In some embodiments of the invention, it is specifically contemplated that the targeting molecule or poly(T)/poly(U) nucleic acid is not labeled with a compound that allows it to be detected, such as a radioisotope, or calorimetric label/fluorophore, as many embodiments of the invention are directed to isolation and not detection of the targeted molecule with a targeting molecule. The term "incubate" refers to maintaining components under certain conditions. The components described herein may also be admixed, mixed, combined, blended, or commingled.

Compositions and methods of the invention involve an isostabilizing agent such as an ion or salt. An isostabilizing agent refers to a solute that affects the hybridization between complementary regions of nucleic acids in such a way that, at certain concentrations of the solute, they negate the difference in the hydrogen bonding between adenine-thymine/uridine (A-T/U) and guanine-cytidine (G-C) base pairs. In some embodiments of the invention tetramethylammonium (TMAC) or tetraethylammonium chloride (TEAC) is specifically contemplated as the isostabilizing agent. In another embodiment betaine is the isostabilizing agent. In still further embodiments, the isostabilizing agent is triethylamine hydrochloride, quinuclidine hydrochloride, or 1,1'-spirobypyrrolidnium bromide. The isostabilizing agent may be added to a sample directly or it may be provided to the sample as a solution containing other components. The isostabilizing agent may be in a binding solution (which facilitates hybridization between the targeted nucleic acid and the component that selects the targeted nucleic acid), wash solution, or elution solution. Other components of the solutions may include buffers, water, detergents, and other salts. In some embodiments, it is specifically contemplated that certain anions, particularly chaotropic anions, are absent from any solution.

In some embodiments of the invention, the concentration of the isostabilizing agent in a composition comprising a sample and a poly(T) nucleic acid is between about 1.0 M and about 3.0 M, between about 1.2 M and about 2.4 M, or between about 1.5 M and about 2.0 M. In some embodiments, the concentration of the isostabilizing agent in a composition comprising a sample that is incubated under hybridization conditions is about 2.0 M. As discussed above, the isostabilizing agent may be provided to the sample as a binding solution; the concentration of the isostabilizing agent in the binding solution will allow for the concentration of the isostabilizing agent in the composition comprising the sample to be in the ranges discussed above. In some embodiments, the concentration of the isostabilizing agent in a binding solution is "x" times greater than the concentration needed in the composition comprising the sample. Thus, in an embodiment in which the concentration of the isostabilizing agent in composition comprising the sample is about 2.0 M, a 2× binding solution comprises an isostabilizing agent in a concentration of about 4.0 M, a 3× binding solution comprises an isostabilizing agent in a concentration of about 6.0 M, etc. Thus, in some embodiments of the invention, a component is provided to the sample in a concentrated form that allows it to be diluted so as to achieve the proper final concentration so as to achieve a desired effect.

A detergent may be added to a composition comprising the sample or it may be comprised in a binding solution that is incubated with the sample. In any of the embodiments of the invention, it is contemplated that a component may be added directly to a composition containing the sample or it may be provided to the sample in a solution. In some embodiments, the detergent is CHAPS or Triton X-100. The final concentration of CHAPS in the composition may be between about 0.5% and about 2.0%, while the final concentration of Triton X-100 in the composition is between about 0.01% and about 0.1%. A final concentration of about 0.017% for the detergent is specifically contemplated, particularly with respect to Triton X-100. A detergent may be included in the binding, wash, or elution solution. In some embodiments, a detergent is specifically contemplated in the binding solution, and thus, it may be absent from the wash or elution solution. Furthermore, while cations other than the isostabilizing agent may be present in the binding, wash, or elution solution, the absence of such cations in such solutions is also specifically contemplated. For example, in some embodiments, Tris is absent in the binding solution.

The sample may be any composition that contains mRNA, including tissue or cell lysate, which refers to a composition of substances from the lysis of cells (or cells from a tissue). Methods of the invention may further comprise steps for preparing a tissue lysate for subsequent mRNA isolation using the method described herein. The use of lysate preparation protocols is specifically contemplated, including the use of guanidinium isothiocyanate for preparing a lysate. Furthermore, in some embodiments, a non-reacting structure such as glass may be employed for lysate preparation, to facilitate the use of methods and compositions for isolating mRNA described herein.

A poly(T) or poly(U) nucleic acid molecule refers to a nucleic acid composed of either RNA or DNA, though a poly d(T) nucleic acid molecule is specifically contemplated. Embodiments discussed with respect to a poly d(T) nucleic acid molecule apply with respect to a poly(T) RNA nucleic acid as well. Such a nucleic acid molecule comprises 1) at least 50% "T" and/or "U" residues across the entire molecule, though a nucleic acid molecule comprising greater than 70% or 100% "T" and/or "U" residues is specifically contemplated as part of the invention or 2) comprises a stretch of contiguous "T" and/or "U" residues of at least 14 nucleobases, though a stretch of at least 25, 50, or 100 contiguous "T" and/or "U" residues is specifically contemplated. The use of a poly(U) nucleic acid molecule may be used in place of a poly(T) nucleic acid and vice versa. As discussed above, other components instead of a poly(T) or poly(U) nucleic acid molecule may be employed to target a subset of poly(A) RNA molecules or non poly(A) RNA molecules; such components will similarly use hybridization to isolate such molecules.

In some embodiments of the invention, a composition comprising a sample, poly(dT) nucleic acid molecule, and an isostabilizing agent may first be heated at a temperature between about 60° C. and about 90° C., or between about at least 70° C. and about 90° C., prior to incubation under hybridization conditions. Temperatures of about 60° C., 70° C., 80° C., and 90° C. are specifically contemplated. In some embodiments, hybridization conditions comprise incubating the composition between about 15° C. and 50° C. for at least 3 minutes to 48 hours, or at least 10 minutes to 48 hours, though longer times are contemplated insofar as substantial RNA degradation does not occur. In additional embodiments, incubation time for hybridization is at least 20 minutes, 1 hour, 4 hours, or 8 hours. During hybridization or binding, the sample may be gently rocked. Furthermore, in some embodiments, the binding solution or a solution containing an isostabilizing agent is discarded and additional solution added to the sample; this may be done multiple times.

Methods of the present invention also include a wash step in some embodiments. Poly(A) RNA may be washed one, two, three, four, five, six, seven, eight, nine, ten, or more times. The wash step may be implemented before or after excess liquid from the sample and/or binding solution is removed. The wash step involves incubating the poly(dT) nucleic acid and poly(A) RNA hybridized to it with a wash solution. In some embodiments, the wash solution contains an isostabilizing agent, such as TMAC or TEAC in a concentration less than its concentration in the composition exposed to hybridization conditions or in the binding solution. The final concentration of the isostabilizing agent during a wash step of a composition comprising poly(A) RNA will be about 0.05 M to about 3.0 M; in some embodiments, the final concentration is below about 0.5 M (low salt wash solution), while in others it is greater than about 2.0 M (high salt wash solution) (medium salt wash solution is between 0.5 M and 2.0 M). A final concentration of the isostabilizing agent during the wash step is specifically contemplated to be 0.4 M. In a specific embodiment the poly(dT) or poly(U) nucleic acid molecule and the hybridized poly(A) RNA are washed at least once in a wash solution with an isostabilizing agent concentration greater than about 1.2 M and at least once in a wash solution with an isostabilizing agent concentration of less than about 0.5 M. In further embodiments, a sample is washed with a low, medium, and/or high salt wash solution. As discuss above, the wash solution may be diluted from a higher concentration, for example, 2× (or 2x) concentration, to a final concentration of 1×. Thus, for example, in one embodiment of the invention, a 2×binding solution containing 4 M TMAC and 0.035% Triton X-100 is mixed with an equal volume of sample to achieve a final concentration for hybridization reaction of 2 M TMAC and 0.017% Triton X-100. In many embodiments of the invention, the final concentration of an isostabilizing agent during the binding step is higher than the final concentration of an isostabilizing agent during the wash step.

While the invention is specifically contemplated to omit guanidinium isothiocyanate, a reagent frequently used with RNA isolation, in some embodiments, guanidinium is included in the binding step/solution, wash step/solution, or elution step/solution of the isolation method/compositions. The final concentration of guanidinium in a composition containing poly(A) RNA is between about 0.4 M and about 2.0 M.

A poly(dT) or poly(U) nucleic acid may be a synthetic oligonucleotide. In some embodiments, the oligonucleotide is linked, covalently in some embodiments, or physically attached to a non-reacting structure. In other cases, the oligonucleotide is labeled with a compound that reacts with a second compound physically or covalently linked to a non-reacting structure. A "non-reacting structure" refers to a substance that does not chemically react with the targeted molecule—mRNA—so it can be used to aid in separating the targeted molecule from non-targeted molecules. In some embodiments the non-reacting structure is immobilized. In other embodiments, the non-reacting structure is a bead, cellulose, particulate solid, or other matrix. The bead used may be glass or plastic, and it may be synthetic and/or magnetized. If it is magnetized, the bead may be used in conjunction with a magnetic field. Furthermore, in some embodiments, the non-reacting structure and sample may be centrifuged, filtered, dialyzed, or captured (with a magnet). When the structure is centrifuged it may be pelleted or passed through a centrifugible filter apparatus. The structure may also be filtered, including filtration using a pressure-driven system. Any number of ways of separating or isolating a non-reacting structure may be employed.

In some embodiments, the targeting molecule such as a poly(dT) may be biotinylated or otherwise labeled so as to facilitate isolation. Because biotin reacts with avidin/streptavidin, avidin or streptavidin may be employed in conjunction with a biotinylated substance. The avidin or streptavidin may be linked to a non-reacting structure, such as beads or the surface of a microtiter plate. The non-reacting structure may then be separated from the remainder of the sample to isolate the biotinylated targeting molecule, which itself is bound to the targeted molecule. Thus, in some embodiments, a biotinylated oligo-dT may be employed in conjunction with streptavidin beads to isolate poly(A) RNA molecules. The beads may then be physically separated from the sample to isolate the poly(A) RNA. In some embodiments, a peptide nucleic acid molecule (PNA) may be used as the targeting molecule.

In some embodiments, the method further comprises washing the non-reacting structure before or after exposure to a sample containing RNA, or it may be blocked prior to incubation with a sample by employing a substance that reduces non-specific binding, such as tRNA. Such substances include polymers such as ficoll, polyvinulpyrrolidine, heparin, or dextran sulfate.

Additional embodiments of the methods described herein include a step in which poly(A) RNA is eluted or separated from a non-reacting structure or a molecule (such as streptavidin) linked to the non-reacting structure. The targeted molecule may be eluted with an eluting solution having low ionic strength, which refers to a net concentration of positive or negative charges of less than 0.01 equivalents/L. The eluting solution may include a chelating salt. The eluting solution may have buffers such as Tris and/or EDTA. In some embodiments, the eluting solution includes sodium citrate, which may be in a concentration in the eluting solution of about 0.1 mM to 2 mM, or EDTA-2 Na in a concentration between about 0.1 and 1 mM. Following elution, mRNA may be collected; in some embodiments, the RNA is precipitated using standard salt/alcohol precipitation or it is collected using a column, matrix, or filter for concentrating a nucleic acid.

While many embodiments of the present invention concern mRNA or poly(A) RNA, it is contemplated that the present invention can be implemented with respect to other RNA species (tRNA or rRNA) or a subset of poly(A) RNA. For example, methods and compositions of the invention may be used to separate mRNA from other RNA species in order to purify the other RNA species; that is, mRNA may be isolated away from rRNA, so that the rRNA population is more purified.

Other embodiments of the invention are directed to compositions for achieving purification or isolation of nucleic acid molecules. Kits containing such compositions are specifically contemplated as part of the invention. Compositions and/or apparatuses in the kit would be in a suitable container means, which refers to a container that allows the composition and/or apparatus to be stored and used in methods of the present invention. The container may include synthetic material, or it may include glass material. Kits of the present invention may include one or more of the following:

1) binding solution;
2) wash solution;
3) elution or eluting solution;
4) detergent;
5) poly(dT) oligonucleotide;
6) non-reacting structure;
7) capture device; and
8) RNase inhibitor.

In some embodiments, a poly(dT) oligonucleotide is provided. The poly(dT) oligonucleotide may be linked chemically or physically to a non-reacting structure, which may be cellulose or some other particulate structure. Alternatively, the oligonucleotide may be biotinylated and an avidin/streptavidin-coupled non-reacting structure provided, such as avidin/streptavidin beads. The beads may be plastic, glass, and/or magnetized. If the beads are magnetized, a magnet is included in some embodiments of the invention, such as in the form of a magnetic stand. The kit may contain a binding solution, a wash solution, and/or an elution solution that includes an isostabilizing agent, such as TEAC or TMAC, in various embodiments. Embodiments of these solutions with respect to the methods of the invention pertain to kit embodiments as well. As discussed above, solutions may be provided in a kit in a concentration that is a factor "x" greater than the final concentration of components in the solution that are needed to effect purification of poly(A) RNA. In some embodiments of the invention, the solution is a 2×, 5×, or 10× solution, though in some embodiments, a solution containing an isostabilizing salt, such as the binding solution, is in a concentration of no greater than about 3×.

Also as discussed above, components in the binding or wash step may be added to a composition containing sample as a solution with other components or it may be added individually, or at least initially separate from an isostabilizing agent, to the composition. For example, a detergent such as Triton X-100 or CHAPS may be included in a binding solution of the kit or it may be provided in the kit simply as a detergent solution that is added to a composition in addition to binding solution. Individual components may also be provided in a kit in concentrated amounts; in some embodiments, a component is provided individually in the same concentration as it would be in a solution with other components, such as 2×, 5×, or 10×. It is specifically contemplated that the concentration of the isostabilizing agent in the binding solution is between about 1.0 M and about 5.0 M, is about 4.0 M, or is about 2.0 M. Also specifically contemplated is a wash solution with an isostabilizing agent concentration of between about 0.1 M and 2.0 M. In some embodiments of the invention, the binding or wash solution may include guanidinium isothiocyanate, though in some embodiments this chemical is specifically contemplated to be absent. The concentration of guanidinium may be between about 0.4 M and about 3.0 M In some embodiments of the invention, an elution solution is provided. The elution solution may constitute water or TE, or it may contain sodium citrate. An example of a TE solution is 10 MM TrisCl and 1 mM EDTA, pH 7.5. The solution may have a low ionic strength. In additional embodiments, sodium citrate is included in an elution solution or is included in the kit separate from an isostabilizing agent. The concentration of the salt in the elution solution is, in some embodiments, between about 0.1 mM and about 100 mM.

In so me embodiments, the concentration of the detergent in the binding solution is between about 0.001% to about 1.0%. Alternatively, detergent may be provided individually in a solution at a concentration of between about 0.001% and about 10.0%. Any solution of the kit may further comprise a buffer such as Tris, phosphate, or any "Good" buffer (Ferguson et al., 1980, specifically incorporated by reference, describing such buffers).

Other embodiments of the invention include kits containing devices or apparatus for physically separating the targeted molecule from the remainder of the sample ("capture devices"). A magnetic stand is a capture device of the present invention. Other embodiments include centrifugation as a capture means, as well as a filtration device useable with either differential air pressure or centrifugal force. Other devices that may be used are a microtiter plate format with oligo-dT directly attached to the plate or attached through a biotin-streptavidin/avidin linkage.

Specifically contemplated is a kit containing a poly(dT) oligonucleotide linked to cellulose; hybridization solution comprising tetramethylammonium (TMAC) in a concentration of between about 2 M and 4 M and Triton X-100 in a concentration of between about 0.01% and about 0.1%; wash solution comprising TMAC in a concentration of about 0.4 M; and elution solution comprising sodium citrate in a concentration of between about 1 mM and about 2 mM.

Also specifically contemplated is a kit containing: a poly (dT) oligonucleotide linked to beads, of either a magnetic or nonmagnetic nature; hybridization solution comprising TMAC in a concentration of between about 2 M and 4 M and Triton X-100 in a concentration of between about 0.01% and about 0.1%; wash solution comprising TMAC in a concentration of about 0.4 M, and an elution solution comprising sodium citrate in a concentration of between about 1 mM and about 2 mM.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
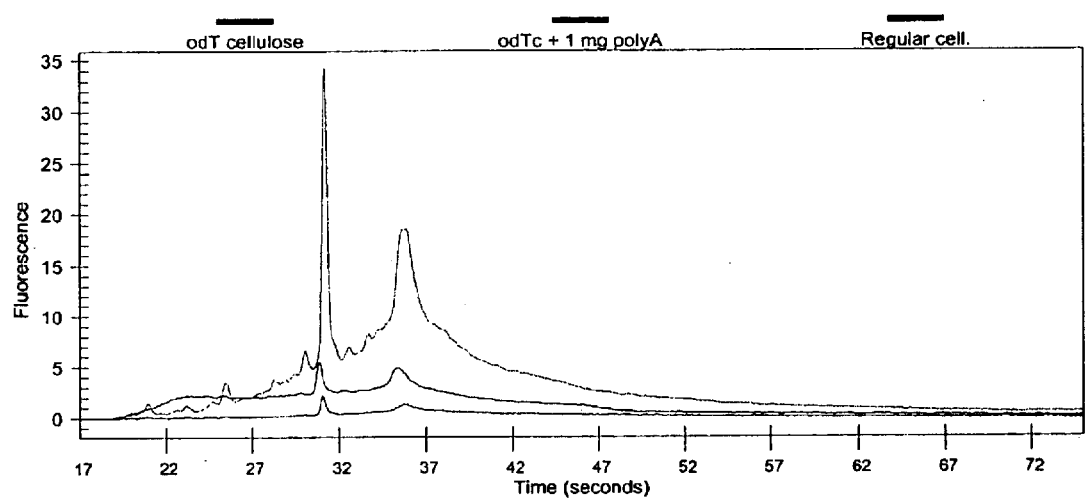
FIG. 1. Comparison of RNA obtained from a standard oligo-dT purification and a similar purification performed in the presence of excess polyA or done on cellulose that has not had oligo-dT attached to it. The profiles were obtained from an Agilent Bioanalyzer, which provides a capillary electrophoretic profile indicating RNA concentration (as indicated by the fluorescence number on y-axis) vs. length (the time of elution, x-axis). All profiles represent the amount of material separated from 5 µg total RNA after a single-passage over whatever separation matrix was used. The most intense profile represents a standard oligo-dT cellulose procedure, the next most intense profile the same procedure performed in the presence of 50 µg polyA (Sigma Chemical Co.), and the minor profile that from the same procedure performed on plain cellulose. Areas under the curve can be used to estimate amounts. The two large peaks seen all profiles are the 18S (left) and 28S (right) rRNA species. The straight oligo-dT cellulose procedure yielded ~1.36 µg of material with 22% rRNA, while the procedure with polyA competitor resulted in approximately 605 µg gross mass, 0.142 µg of which was natural (not polyA) RNA, with 34% rRNA. The use of (non-modified) plain cellulose yielded 0.113 µg with the approximately 22% rRNA.

The present invention concerns methods and compositions (including kits) for isolating and/or purifying poly(A) RNA. It takes advantage of the observations that an isostabilizing agent such as TMAC, TEAC, or betaine reduces binding between non-mRNA and mRNA.

I. RNA

There are generally three types of RNA molecules: messenger RNA (mRNA), transfer RNA (tRNA), and ribosomal RNA (rRNA). The study of RNA occupies a central role in molecular biology. This molecule performs many different functions in the cell. mRNA, which conveys information from the nucleus to the cytoplasm, is the most intensely studied. Several molecular biology procedures use purified mRNA as starting material. These procedures include: cDNA synthesis (for library construction, RT-PCR analysis, or 5' end analysis through primer extension); Northern blot analysis; ribonuclease protection assays; and screening procedures involving in vitro translation. There are several existing procedures to purify RNA from various biological samples. However, mRNA represents only 1–5% of the mass of total RNA (Sambrook, 2001). Of the remainder, the major RNA species is ribosomal RNA (rRNA), constituting 80% or more of total RNA mass (Sambrook et al., 1989 and 2001). Although the total RNA isolated from cells can sometimes be used for the above-mentioned procedures, usually a preliminary purification of mRNA from total RNA is often preferred, if not required. This is especially true if the particular mRNA being sought or targeted is in low abundance (0.5% or less of the mRNA population). The presence of rRNA can interfere in the detection of mRNA by Northern blotting, RNase protection assays, differential display analysis, and expression profiling by gene arrays, especially if the target being analyzed is in low abundance. Often, the mRNA from scientifically interesting genes fall into this category.

II. Components and Reagents

The present invention is directed at methods and compositions for isolating and purifying RNA populations, particularly mRNA. A number of components and reagents are contemplated for use in the methods of the invention and as part of the compositions of the invention. In addition, solutions may contain buffers such as Tris, phosphate, or other appropriate buffers for RNA in addition to preservatives, however, in some embodiments the buffer is specifically contemplated to be absent.

A. Isostabilizing Agents

Isostabilizing agents equalize hydrogen bond strengths between basepairing residues, specifically A:T/U and G:C. Thus, any increased affinity between G and C residues as compared to A and T residues (between the poly(A) tail of mRNA and an oligo-dT) is minimized in the presence of an appropriate concentration of an isostabilizing agent. Isostabilizing agents include tetraalkylammonium salts such as tetramethylammonium ($TMA^+$) cations and tetraethylammonium ($TEA^+$) cations. While tetrabutylammonium or tetrapropylammonium or other ions may be employed to practice the present invention (Shapiro et al., 1969), TEAC and TMAC are implemented in many embodiments of the invention, as are triethylamine hydrochloride, quinuclidine hydrochloride, and 1,1'-spirobypyrrolidnium bromide.

An "effective amount" of an isostabilizing agent reduces binding of unwanted RNA, or non-targeted RNA, to the targeting or targeted agent, without significantly affecting specific binding between the targeting and targeted agents. In many embodiments of the invention, the non-targeted RNA is rRNA. Appropriate final concentrations of an isostabilizing agent are about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 M, or more; alternatively, final concentrations of an isostabilizing agent are between about 0.1 M to about 5.0 M, between about 0.5 M to about 4.5 M, between about 1.0 to about 4.0 M, between about 2.0 M to about 3.0 M, between about 0.6 M and 3.0 M, between about 3.0 M and about 4.5 M, and between about 1.2 M and about 2.4 M. In addition final concentration may be greater than 0.5 M, 1.0 M, 1.5 M, 2.0 M, 2.5 M, 3.0 M, 3.5 M, or 4.0 M. Final concentrations of about 3.0 M of TMAC and about 2.4 M TEAC are specifically contemplated during hybridization between the targeting and targeted agents. Solutions made with an isostabilizing agent that are added to a sample may have concentrations of the isostabilizing agent that are about 1.5×, 2×, 2.5×, 3×, 3.5×, 4×, 4.5×, 5×, 6×, 7×, 8×, 9×, 10×, or more times greater than the final concentration desired. These x-fold concentrations encompass any solution of the invention—binding, wash, and elution—in addition to concentrations of components added to a sample apart from a solution containing an isostabilizing agent.

B. Detergents

Detergents may be used to facilitate mRNA purification. These detergents specifically include Triton X-100 and CHAPS. CHAPS is the zwitterionic detergent 3-[(3-cholamidopropyl)-dimethylammonio]-1-propanesulfonate.

Detergents may be ionic or nonionic. Examples of nonionic detergents include triton, such as the Triton X series (Triton X-100, Triton X-100R, Triton X-114, Triton X-450, Triton X-450R), octyl glucoside, polyoxyethylene(9) dodecyl ether, digitonin, IGEPAL CA630, n-octyl-beta-D-glucopyranoside (betaOG), n-dodecyl-beta, C12EO7, Tween 20, Tween 80, polidocanol, n-dodecyl beta-D-maltoside (DDM), NP-40, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), and cetyltrimethylammoniumbromide (CTAB). A zwitterionic reagent may also be used in the purification schemes of the present invention, such as Chaps, zwitterion 3–14, and 3-[(3-cholamidopropyl) dimethylammonio]-1-propanesulfonate.

C. Targeting Agents

Targeting agents include molecules that are employed to isolate a targeted substance, such as mRNA. A nucleic acid molecule is used as the targeting agent in many embodiments. They may take advantage of complementarity between nucleic acid molecules. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. An oligonucleotide may comprise or be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 92, 93, 94, 95, 96, 97, 98, 99 nucleobases in length.

A nucleic acid "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

A poly(dT) nucleic acid, for example, refers to a nucleic acid molecule comprising DNA that has more than 90% T residues or comprising a DNA region of at least 10 contiguous T residues. An "oligo-dT," which is used as a targeting agent for poly(A) RNA, refers to a synthesized DNA oligonucleotide of which greater than 90% is the nucleobase T. It is contemplated that analogs of the nucleobase T or U may be used insofar as they allow for hybridization between T/U and A residues.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof A nucleobase may be comprised in a nucleoside or nucleotide, using any chemical or natural synthesis method described herein or known to one of ordinary skill in the art.

2. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

3. Polyether and Peptide Nucleic Acids (PNA)

In certain embodiments, it is contemplated that a nucleic acid comprising a derivative or analog of a nucleoside or nucleotide may be used in the methods and compositions of the invention. A non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid," also known as a "PNA," "peptide-based nucleic acid analog," or "PENAM," described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

4. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

5. Hybridization

As used herein, "hybridization," "hybridizes," or "capable of hybridizing" is understood to mean the forming of a double or triple stranded molecule or forming regions that are double or triple stranded in nature. The term "anneal" as used herein is synonymous with "hybridize."

As used herein "stringent condition(s)" or "high stringency" are those conditions that allow hybridization between or within one or more nucleic acid strand(s) containing complementary sequence(s), but precludes hybridization of non-complementary sequences. Stringent conditions tolerate little, if any, mismatch between a nucleic acid and a target strand. Such conditions are well known to those of ordinary skill in the art, and are preferred for applications requiring high selectivity.

D. Non-Reacting Structures

A non-reacting structure may be employed in the context of the invention to facilitate mRNA isolation or purification. In some embodiments targeting molecule may be chemically or physically attached to a non-reacting structure. An example of this is oldigo-dT coupled to cellulose. Alternatively, a non-reacting structure may be attached to a compound, such as avidin or streptavidin, that binds with a substance on the targeting molecule, such as biotin.

1. Cellulose

Cellulose is a structural polymer derived from vascular plants. Chemically, it is a linear polymer of the monosaccharide glucose, using $\beta$, 1–4 linkages. Cellulose can be provided commercially, including from the Whatman company, and can be chemically sheared or chemically modified to create preparations of a more fibrous or particulate nature. CF-1 cellulose from Whatman is an example that can be implemented in the present invention.

2. Beads

Synthetic plastic or glass beads may be employed in the context of the invention. The beads may be complexed with avidin or streptavidin and they may also be magnetized. The complexed streptavidin can be used to capture biotin linked to an oligo-dT or -U or poly (dT) or poly(U) moiety, either before or after hybridization to the poly(A) tails of mRNA. Alternatively, the oligo/poly(dT/U) moiety can be attached to the beads directly through chemical coupling. The beads may be collected using gravity- or pressure-based systems and/or filtration devices. If the beads are magnetized, a magnet can be used to separate the beads from the rest of the sample. The magnet may be employed with a stand or a stick or other type of physical structure to facilitate isolation.

E. Other Components

Other components include isolation apparatuses such as filtration devices, including spin filters or spin columns.

F. Kits

All the essential materials and/or reagents required for isolating or purifying mRNA from a sample may be assembled together in a kit. This generally will comprise a targeting agent such as biotinylated oligo-dT, oligo-dT coupled to plastic or glass beads, or oligo-dT-cellulose designed to hybridize specifically to poly(A) mRNA. Also included are solution(s) and/or component(s) to provide the necessary reaction mixture for hybridization and isolation. Such kits may also include components that facilitate isolation of the targeting molecule, such as filters, beads, or a magnetic stand. Such kits generally will comprise, in suitable means, distinct containers for each individual reagent or solution as well as for the targeting agent.

A kit will also include instructions for employing the kit components as well the use of any other reagent not included in the kit. Instructions may include variations that can be implemented.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

PolyA RNA Purification Using Oligo dT Cellulose and TMAC

1. Mix up to 0.5 ml of RNA (0.4–2 mg) in water or TE with an equal volume of 4 M TMAC and 1/600$^{th}$ final volume of 10% Triton X-100 (termed "2×Binding Solution").
2. Add this mixture to 0.1 g oligo dT cellulose.
3. Incubate the samples at 75° C. for 5 minutes.
4. Incubate the samples with gentle rocking for one hour at room temperature.
5. Pre-warm elution buffer (1 mM to 75° C.).
6. Spin down the oligo dT cellulose (OdTc). Remove supernatant.
7. Resuspend the OdTc in 500 μl 2 M TMAC (termed "Wash Solution 1"). Mix thoroughly. Spin down and discard supernatant.
8. Resuspend the OdTc in another 500 μl 2 M TMAC. Mix thoroughly. Transfer to spin filter. Centrifuge at 5000×G for a minute to drive supernatant through.
9. Resuspend the OdTc in 500 μl 0.4 M TMAC (termed "Wash Solution 2"). Mix thoroughly. Transfer to spin filter. Centrifuge at 5000×G for a minute to drive supernatant through.
10. Repeat step 9.
11. Elute with 2 volumes (100–200 μl) of the pre-warmed solution containing 1 mM sodium citrate, pH 6.4 (termed "The RNA Storage Solution").

Example 2

PolyA RNA Purification Using Oligo dT Magnetic Beads and TMAC

Procedure
1. Mix up to 0.5 ml of solution containing 10–1000 μg RNA in water or TE with an equal volume of 4 M TMAC and 1/600$^{th}$ volume of 10% Triton X-100.
2. Remove an aliquot of magnetic beads with a mass equal to that of the total RNA (stocks contain 10 mg magnetic beads per μl of slurry volume; nominal size of 1 μm) and sediment to side of tube using a magnetic stand.
3. Resuspend beads in 2 M TMAC, re-sediment, and repeat.
4. Add the total RNA mixture (in 2 M TMAC+0.017% Triton X-10) to the oligo dT magnetic beads that have been equilibrated with 2 M TMAC.
5. Incubate the samples at 75° C. for 5 minutes.
6. Incubate the samples with gentle rocking for one hour at room temperature.
7. Sediment the oligo-dT magnetic beads (OdTMB) to the side of the tube using a magnetic stand. Remove supernatant.
8. Resuspend the OdTc in 500 μl 2 M TMAC. Mix thoroughly. Sediment the OdTMB to the side of the tube using a magnetic stand and discard supernatant.
9. Resuspend the OdTMB in another 500 μl 2 M TMAC. Mix thoroughly. Sediment the OdTMB to the side of the tube using a magnetic stand and discard supernatant.
10. Resuspend the OdTc in 500 μl 0.4 M TMAC. Mix thoroughly. Sediment the OdTMB) to the side of the tube using a magnetic stand and discard supernatant.
11. Repeat step 10.
12. Elute with 2 volumes (100–200 μl) of the pre-warmed elution buffer (water, TE, or 1 mM Na-citrate). Vortex briefly and pulse spin to collect all of the solution at the bottom of the tube before sedimenting the OdTMB to the side of the tube using a magnetic stand and collecting supernatant.
13. Add 1/10 volume of 3 M sodium acetate to each eluted sample and mix. Add 1 μl (1/200 volume) of glycogen solution to each sample and mix.
14. Add 0.5 ml (2.5 volume) of 100% ethanol to each sample. Mix by inverting several times.
15. Incubate your samples at −20° C. from 30 minutes to overnight.
16. Centrifuge the samples for 30 minutes at full speed in a tabletop centrifuge. The presence of glycogen will ensure a pellet is visible at the bottom of your tube.
17. Remove the supernatant (we recommend through a drawn-out Pasteur pipette).
18. Add 0.5 ml 70% ethanol to each tube. Vortex briefly to wash the pellets.
19. Centrifuge for 5 min. at full speed.
20. Aspirate the supernatant.
21. Resuspend samples in 1 mM Na-citrate, pH 6.4. The exact volume will depend on the input amount and the analysis planned.

When the samples prepared by examples 1 and 2 were compared by ethidium-staining of a denaturing gel, it could be seen that substantially less rRNA was present than equivalent samples from a standard OdT cellulose procedure, even after two-fold repetitive purifications were performed. Furthermore, on examining the presence of three common mRNA species (β-actin, GAPDH, cyclophilin) using the Northern blot technique, the yield was also superior.

Example 3

Testing of Three Variables

The following three variables were tested: (1) NaCl, TEAC, or TMAC; (2) Oligo-dT cellulose or magnetic beads (Seradyn); and (3) With and without heating the binding mixture.

Procedure
1. The purification was performed from 25 μg total mouse kidney RNA.
2. The above (oligo-dT-cellulose and -magnetic bead) procedures were followed, and the procedure was duplicated using TEAC solutions (same concentrations as TMAC) in place of TMAC. As a control, the 'normal' procedure using NaCl as per the AMBION POLY(A) PURE manual was also performed on both the oligo-dT cellulose and on oligo-dT magnetic beads.

3. Each of the 6 samples described in part 1 was run in duplicate. One of these had the binding mixture (RNA, specific salt solution, plus oligo-dT matrix) heated for 5 minutes at 75° C. prior to the 1-hour binding incubation, while the other was maintained at room temperature.
4. Samples were redissolved post-elution in 20 μl water.
5. 5 μl of each was loaded on a denaturing agarose gel,as well as 1 μg of the input total RNA.
6. The gel was Northern-blotted and probed for GAPDH (glyceraldehyde phosphate dehydrogenase, one of the glycolytic pathway enzymes) mRNA, 18S rRNA, and 28S rRNA.
7. The bands for each RNA were quantified using a phosphorimaging system (BIO-RAD). Total signal from the desired GAPDH band was divided by the intensity of the ribosomal RNA bands. These numbers were normalized by dividing by this ration observed in the total RNA input to give an "enrichment index":

Results

Figure 2A:
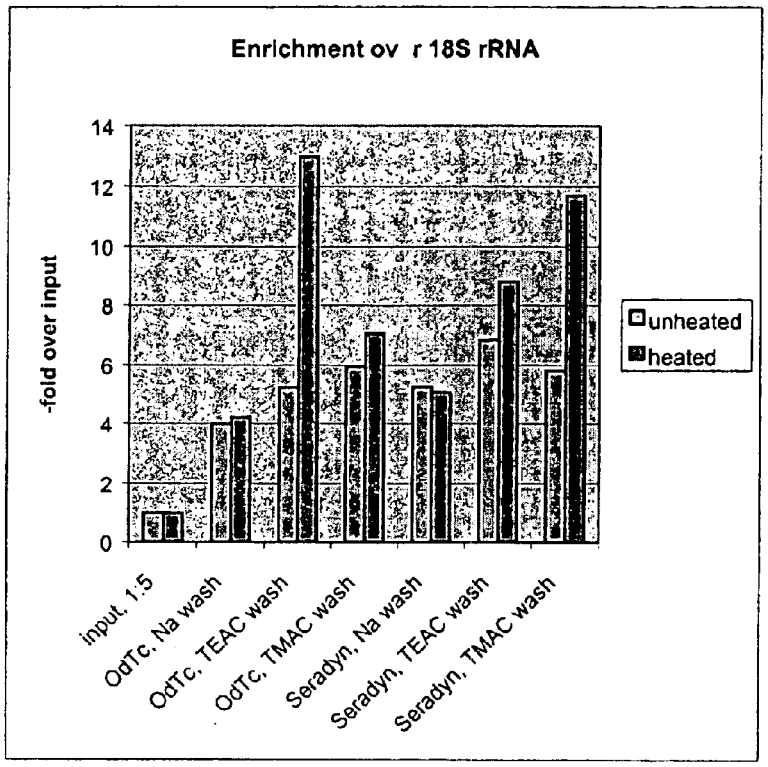
FIG. 2A and 2B. RNA Quantification. The bands for each RNA were quantified using a phosphorimaging system (Bio-Rad). Total signal from the desired GAPDH band was divided by the intensity of the ribosomal RNA bands. These numbers were normalized by dividing by this ration observed in the total RNA input to give an "enrichment index."
Figure 2B:
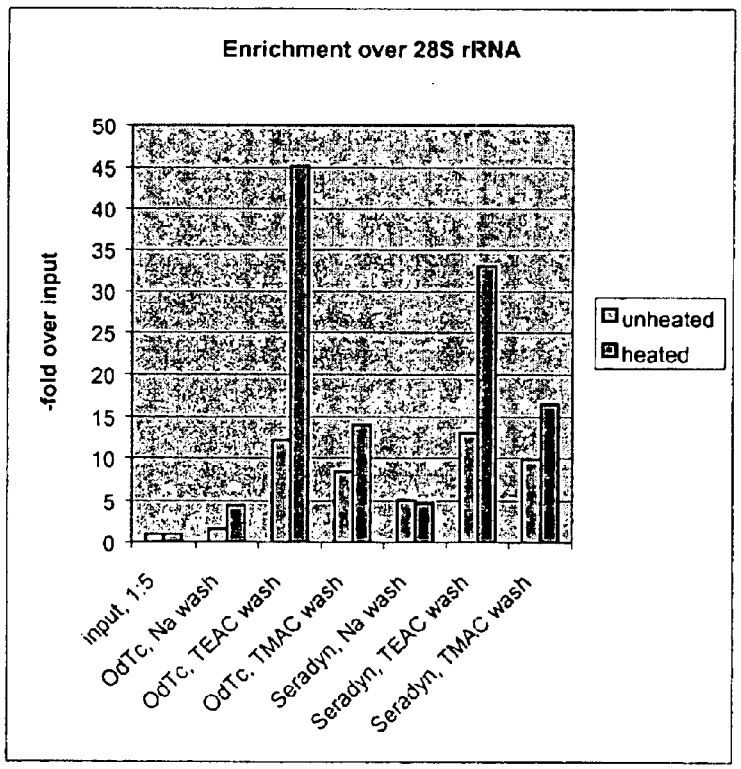

Higher enrichment levels are desirable. In FIGS. 2A and 2B, it can be seen that
1. Both TEAC and TMAC provide an improvement over standard NaCl wash conditions;
2. Heating provides an advantage, particularly with the new salt systems;
3. Both oligo-dT on cellulose and on magnetic beads benefit using this system.

Example 4

Usine the System with PNAs

A biotin-linked peptide nucleic acid was obtained from ACTIVE MOTIF (Carlsbad, Calif.; the TOTAL mVADER kit). For a comparative control, the protocol described in the manual for the kit was followed exactly, except for one aspect: magnetic capture was used for isolating the magnetic streptavidin beads. A second set used the following conditions:
1. binding of mRNA to (poly T) PNA-biotin:
   mix: 100 μg total mouse liver RNA, 2 M TMAC, 0.017% Triton X-100, 15 μl of PNA from mVADER KT
   preheat: 75° C. for 10 minutes
   incubate: 1 hr at room temperature with tumbling
2. add streptavidin beads (45 μl, same as in mVADER protocol), incubate an additional hour at room temperature
3. wash two times with 2 M TMAC, 500 μl each
4. wash two times with 0.4 M TMAC, 500 μl each
5. elute with two 75 μl aliquots of water at room temperature
6. precipitate the RNA in the eluate with 1/10$^{th}$ volume 3 M NaOOCCH$_3$ and 2.5 volumes ethanol. Chill samples to −20° C. overnight.
7. Pellet precipitate and wash pellet with 70% ethanol using standard procedures.
8. Dissove pellets in 20 μl water. Run 5 μl of each on a denaturing agarose gloxal gel.
9. Document ethidium-staining pattern on gel.
10. Transfer gel to membrane using standard Northern blotting procedures. (Given in AMBION NORTHERN MAX kit manual.)
11. Probe northern blot for presence of β-actin, GAPDH, and cyclophilin mRNAs.

Results

The use of TMAC resulted in a substantial reduction in the intensity of the rRNA bands in the ethidiun-bromide-stained gel relative to the standard procedure for the mVADER kit. Even though the ethidium staining was reduced, the levels of the three mRNAS for β-actin, GAPDH, and cyclophilin in the TMAC protocol were equal to those in the standard protocol.

Example 5

Effects of Binding with Triton X-100

The procedures of Examples 1 and 2 above were used to purify polyA$^+$ RNA from total mouse liver RNA. 100 μg of the RNA was used in four reactions for both the oligo-dT cellulose and oligo-dT magnetic beads. For each matrix, the four samples were split into two replicates of two. One of these followed the above procedures exactly, and the second omitted the presence of Triton X-100 in the binding solution, following all other aspects of the procedure exactly. Samples were precipitated, electrophoresed and Northern blotted as in Example 4 above.

Although the presence of Triton X-100 in the binding reaction had negligible effects on the yield of the mRNAs assayed, the presence of rRNA bands was noticeably lower in the samples that were bound in the presence of Triton X-100. This was dramatically noticeable in the magnetic bead samples, less so in the celllulose ones.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,816,571
U.S. Pat. No. 4,959,463
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,459,253
U.S. Pat. No. 5,466,786
U.S. Pat. No. 5,470,967
U.S. Pat. No. 5,539,082
U.S. Pat. No. 5,554,744
U.S. Pat. No. 5,574,146
U.S. Pat. No. 5,602,240
U.S. Pat. No. 5,602,244

U.S. Pat. No. 5,610,289
U.S. Pat. No. 5,614,391
U.S. Pat. No. 5,614,617
U.S. Pat. No. 5,623,070
U.S. Pat. No. 5,645,897
U.S. Pat. No. 5,652,099
U.S. Pat. No. 5,654,147
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,606
U.S. Pat. No. 5,714,331
U.S. Pat. No. 5,719,262
U.S. Pat. No. 5,736,336
U.S. Pat. No. 5,759,777
U.S. Pat. No. 5,763,167
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
U.S. Pat. No. 6,045,996
EP 266,032
PCT/EP/01219
WO 92/20702
Aviv et al., *Proc. Natl. Acad. Sci. USA* 1972 Jun;69(6):1408–12.
Egholm et al., *Nature*, 365(6446):566–568, 1993.
Ferguson et al., *Anal. Biochem.* 1980 May 15;104(2):300–10.
Froehler et al., *Nuc. Acid. Res.* 1986 Jul 11;14(13):5399–407.
Gitschier et al., *Science* 1986 Jun 13;232(4756):1415–6.
Golas et al., *Chem-Biol. Interact.* 1980;30:209–22.
Jacobs et al., *Nucleic Acids Res* 1988 May 25;16(10):4637–50.
Jacobs et al., *Nature* 1985 Feb 28-Mar 6;313(6005):806–10.
Kuribayashi et. al. *Nuc. Acid Res.* 1988;19:61–64.
Melchior et al., *Proc Natl Acad Sci USA* 1973 Feb;70(2):298–302.
Nguyen et al., *Nucleic Acids Res* 1999 Mar 15;27(6):1492–8.
Rees et al., *Biochemistry* 1993 Jan 12;32(1):137–44.
Sambrook, Fritsch, Maniatis, *Molecular Cloning: A Laboratory Manual*, 2nd Ed., Cold Spring Harbor Press, Cold Spring Harbor, N.Y., 1989.
Sambrook, Fritsch, Maniatis, *Molecular Cloning: A Laboratory Manual*, 3rd Ed., Cold Spring Harbor Press, Cold Spring Harbor, N.Y., 2001.
Scheit, "Nucleotide Analogs," In. *Synthesis and Biological Function*, Wiley-Interscience, New York, pp. 171–172, 1980.
Schott et al., *J Pharm Sci* 1977 Feb;66(2):165–8.
Shapiro et al, *Biochemistry* 1969 Aug;8(8):3233–41
Wood et al., *Proc Natl Acad Sci USA* 1985 Mar;82(6):1585–8.
Wozney, *Methods Enzymol* 1990;182:738–51.

What is claimed is:

1. A method for purifying poly(A) mRNA from a sample in a manner that reduces rRNA carryover comprising:
  a) incubating a composition comprising:
    i) the sample, wherein the sample includes poly(A) mRNA;
    ii) a poly(dT) or poly(U) nucleic acid molecule; and
    iii) tetramethylammonium chloride (TMAC) or tetraethylammonium chloride (TEAC),
    under conditions allowing poly(A) mRNA to hybridize with the poly(dT) or poly(U) nucleic acid molecule and inhibiting partial hybridization of the poly(A) mRNA to any rRNA that may be present in the sample; and
  b) isolating the poly(dT) or poly(U) nucleic acid molecule and the hybridized poly(A) mRNA;
  wherein rRNA carryover is reduced.

2. The method of claim 1, wherein the isostabilizing agent is TMAC, and wherein the nucleic acid molecule is poly(dT) and is linked to a non-reacting structure, and further comprising c) washing the poly(dT) nucleic acid molecule with a wash solution comprising a salt.

3. The method of claim 1, wherein the composition further comprises CHAPS in a final concentration between about 0.5% and about 2.0%.

4. The method of claim 1, further comprising heating the composition at a temperature between about 70° C. and about 90° C. prior to incubation under hybridization conditions.

5. The method of claim 1, wherein the sample or the hybridization solution does not contain guanidinium.

6. The method of claim 1, wherein the TMAC or TEAC is provided to the composition in a hybridization solution.

7. The method of claim 6, wherein the hybridization solution further comprises Triton X-100.

8. The method of claim 1, wherein the composition further comprises Triton X-100.

9. The method of claim 8, wherein the concentration of Triton X-100 in the composition is between about 0.01% and about 0.1%.

10. The method of claim 1, wherein the hybridization conditions comprise incubating the composition between about 15° C. and 50° C. for at least 10 minutes to 48 hours.

11. The method of claim 10, wherein the incubation time is at least 4 hours.

12. The method of claim 1, wherein the poly(dT) or poly(U) nucleic acid molecule is biotinylated.

13. The method of claim 12, further comprising
  c) incubating the biotinylated oligonucleotide and the sample with avidin or streptavidin linked to a non-reacting structure; and
  d) eluting the poly(A) mRNA from the non-reacting structure with an eluting solution.

14. The method of claim 1, wherein the final concentration of the TMAC and/or TEAC in the composition is between about 1.0 M and about 3.0 M.

15. The method of claim 14, wherein the final concentration of the TMAC and/or TEAC in the composition is between about 1.2 M and about 2.4 M.

16. The method of claim 15, wherein the final concentration of the TMAC and/or TEAC in the composition is between about 1.5 M and about 2.0 M.

17. The method of claim 1, further comprising washing the poly(dT) or poly(U) nucleic acid molecule and the hybridized poly(A) mRNA in wash solution comprising TMAC or TEAC.

18. The method of claim 17, wherein the poly(dT) or poly(U) nucleic acid molecule and the hybridized poly(A) mRNA are washed more than once.

19. The method of claim 18, wherein the concentration of the TMAC and/or TEAC in the wash solution is between about 0.05 M and about 3.0 M.

20. The method of claim 18, wherein the poly(dT) or poly(U) nucleic acid molecule and the hybridized poly(A) mRNA are washed at least once in a wash solution with a TMAC and/or TEAC concentration greater than about 1.2 M and at least once in a wash solution with a TMAC and/or TEAC concentration of less than about 0.5 M.

21. The method of claim 1, wherein the poly(dT) or poly(U) nucleic acid molecule is linked to a non-reacting structure.

22. The method of claim 21, wherein the non-reacting structure is cellulose.

23. The method of claim 21, further comprising eluting the poly(A) mRNA from the non-reacting structure with an eluting solution of low ionic strength.

24. The method of claim 23, wherein the eluting solution comprises sodium citrate.

25. The method of claim 21, further comprising isolating the non-reacting structure linked to the oligonucleotide that is hybridized to poly(A) mRNA.

26. The method of claim 25, further comprising washing the non-reacting structure.

27. The method of claim 25, wherein the non-reacting structure is isolated from the sample by centrifugation or filtration.

28. The method of claim 21, wherein the non-reacting structure is a bead.

29. The method of claim 28, wherein the bead is magnetic.

30. The method of claim 29, wherein the poly(dT) or poly(U) nucleic acid molecule and the hybridized poly(A) mRNA are isolated from the sample with a magnet.

31. A method for purifying poly(A) mRNA from a sample in a manner that reduces rRNA carryover comprising:

a) incubating the sample with a poly(dT) oligonucleotide connected to a non-reacting structure and a hybridization solution comprising TMAC and/or TEAC under conditions allowing poly(A) mRNA to hybridize with the oligonucleotide;

b) isolating the oligonucleotide with the hybridized poly(A) mRNA away from the sample; and c) washing the oligonucleotide with a wash solution comprising a salt wherein rRNA carryover is reduced.

32. The method of claim 31, wherein the non-reacting structure is cellulose.

33. The method of claim 31, further comprising eluting the poly(A) mRNA from the non-reacting structure with an eluting solution with low ionic strength.

34. The method of claim 31, wherein the oligonucleotide is biotinylated.

35. The method of claim 34, further comprising c) incubating the biotinylated oligonucleotide and the sample with avidin or streptavidin linked to a non-reacting structure; and d) eluting the poly(A) mRNA from the non-reacting structure with an eluting solution.

36. The method of claim 35, further comprising isolating the non-reacting structure linked to the oligonucleotide hybridized to poly(A) mRNA by centrifugation or filtration.

* * * * *

UNITED STATES PATENT AND TRADEMARK OFFICE
CERTIFICATE OF CORRECTION

PATENT NO. : 6,812,341 B1
DATED : November 2, 2004
INVENTOR(S) : Richard C. Conrad It is certified that error appears in the above-identified patent and that said Letters Patent is hereby corrected as shown below:

Column 20,
Line 5, delete "i) the" and insert -- i) a --.
Lines 17-18, delete "the isostabilizing agent is" and insert -- the composition comprises --.
Lines 26 and 27, after "°C" delete ".".
Lines 29-30, delete "the hybridization solution" and insert -- the composition --.
Line 47, delete "olgionucleotide" and insert -- nucleic acid molecule --.

Signed and Sealed this

Nineteenth Day of April, 2005

JON W. DUDAS
*Director of the United States Patent and Trademark Office*